United States Patent [19]

Uemura et al.

[11] Patent Number: 5,319,072
[45] Date of Patent: Jun. 7, 1994

[54] HUMAN ANTITHROMBIN-III PREPARATION

[75] Inventors: Yahiro Uemura, Arcadia; Swaraj Kaur, Montclair; Prabir Bhattcharya, Walnut, all of Calif.

[73] Assignee: Alpha Therapeutic Corporation, Los Angeles, Calif.

[21] Appl. No.: 818,831

[22] Filed: Jan. 10, 1992

[51] Int. Cl.$^5$ .................. C07H 1/00; C08B 37/10; C07K 15/06
[52] U.S. Cl. ................. 530/393; 536/124; 536/54; 536/21; 436/16; 436/161
[58] Field of Search .......... 514/56, 8; 530/413, 530/382, 393; 436/16, 161; 536/21; 210/656

[56] References Cited

U.S. PATENT DOCUMENTS 4,632,981 12/1986 Bock et al. ................. 514/8
5,066,788 11/1991 Reutelingsperger .......... 530/381

OTHER PUBLICATIONS

*Biochemical and Biophysical Research Communications,* vol. 61, No. 4, 1974, "Purification of Canine Antithrombin III-Heparin Cofactor Using Affinity Chromatography" Damus et al.
*Thrombosis Research,* vol. 5, pp. 439–452, 1974 Miller-Anderson et al.
*British Journal of Haematology,* 31, 1975, pp. 233–243 Thaler et al.
*Vox Sang,* 36:281–293 (1979) Wickerhauser et al.
Rybak et al.; Chemical Abstracts 96:1580306.
Hoogendoorn et al.; Thrombosis Research 20:7783 (1983).
Kirkwood et al.; Chemical Abstracts 93:643016 (1980).
Eibi et al.; Chemical Abstracts 102:119615u (1985).
Jap. Red. Cross, Chemical Abstracts 103:42631g (1985).

*Primary Examiner*—Johnnie R. Brown
*Assistant Examiner*—Kathleen Kahler Fonda
*Attorney, Agent, or Firm*—Sughrue, Mion, Zinn, Macpeak & Seas

[57] ABSTRACT

A method for purifying human antithrombin III in an alcoholic solution at low temperature using bound heparin is provided.

15 Claims, No Drawings

HUMAN ANTITHROMBIN-III PREPARATION

FIELD OF THE INVENTION

The invention relates to a method for preparing human antithrombin-III.

BACKGROUND OF THE INVENTION

Antithrombin-III (AT-III) is an $\alpha_2$globulin known to inhibit the coagulation of blood. AT-III acts essentially as an irreversible inhibitor. It is believed that AT-III inhibits serine proteases in plasma during the activation of either the coagulation or the fibrinolytic systems. AT-III has significant inhibitory activity of factor Xa and thrombin.

Families congenitally deficient in AT-III have a high incidence of thromboses. Administration of AT-III to patients with thrombotic disorders has been attempted.

There are reports of attempts to purify AT-III from human plasma and plasma pastes using conventional techniques. However, those procedures were lengthy or the yields were poor. A substantial improvement in the purification methodology took place with the incorporation of an affinity chromatography step using purified heparin as the solid phase bound ligand.

Damus & Wallace (*Biochem. Biophys. Res. Comm.*, 61 (4); 1147, 1974) purified canine AT-III in a scheme that incorporated heparin-Sepharose chromatography. Heat defibrinated plasma was passed over a small column containing heparin-Sepharose at 8° C. The end product was still heterogeneous as determined by the distribution of specific activity throughout the elution profile.

Miller-Andersson et al. (*Thromb. Res.*, 5:439, 1974) teaches the use of heparin-Sepharose to purify human AT-III. Citrated human plasma that had been frozen immediately after removal of blood cells by centrifugation was added in batch fashion to heparin-Sepharose at 5° C. The gel suspension then was poured into a column, allowed to settle and the adsorbed material was eluted with a salt gradient. The entire procedure, which included ion exchange and gel filtration chromatography, provided a 34% yield. The large number of chromatographic separations minimizes the possibility of large scale production of AT-III by that method.

Thaler & Schmer (*Br. J. Haemat.*, 31:233, 1975) described an isolation procedure for human and bovine AT-III that involved heparin-agarose chromatography and polyethylene glycol precipitation. All procedures were carried out at 4° C. Either chromatography or precipitation can serve as the initial step in the purification scheme.

Wickerhauser et al. (*Vox Sang.*, 36:281, 1979) describes a large scale method for the preparation of AT-III from plasma or from Cohn fraction IV-VI. The method begins with a polyethylene glycol precipitation followed by batch adsorption on heparin-Sepharose, desalting by ultrafiltration and followed by pasteurization of the final product. The recovery by activity was 32% from plasma and 16% from Cohn fraction IV. All purification steps were carried out at 5° C.

SUMMARY OF THE INVENTION

An object of the instant invention is to provide a simple, robust method for purifying human AT-III present in an ethanol-containing solution.

A further object of this invention is to adapt AT-III purification methods in which immobilized heparin is employed as a ligand to ethanol solutions containing AT-III.

Still another object of this invention is to provide a purified AT-III from Cohn's fractions II+III supernatant.

The above and other objects have been achieved by providing a method in which an alcoholic solution containing AT-III such as an ethanolic human plasma supernate is exposed to a heparin affinity gel matrix at temperatures below 4° C. Preferably, the process temperature is below 0° C.

DETAILED DESCRIPTION OF THE INVENTION

An alcohol-containing human plasma fraction is a suitable starting material for this invention. Cohn's fractions II+III supernatant is a preferred starting material. Cohn's fractions II+III supernatant contains about 20% ethanol.

The heparin is monomeric heparin which is coupled to insoluble solid supports comprised of, for example, polysaccharide, silica gel or fibers. Examples of such solid supports are agar, agarose, cross-linked agarose, cellulose, silica, nylon and the like as is known in the art.

The purification is obtained by exposing the alcoholic plasma fraction to the heparin gel matrix at temperatures of about +3° C. to about −10° C. and preferably at temperatures below 0° C. Particularly preferred is a purification conducted at −6° C.

If the purification is conducted in a batch process, ligand bound AT-III can be removed from the II+III supernatant-gel matrix mixture by conventional methods, such as centrifugation.

The AT-III is eluted from the heparin-gel matrix by conventional methods, such as exposure to high salt buffers, for example 2 M NaCl.

Optionally, the purified AT-III solution can be treated by heat, for example, at about 60° C. for about 10 hours in about 0.2M to about 0.6M citrate buffer at a pH of about 7 to about 8, or with detergent, for example, exposure to detergent at about 20° C. to about 40° C. for about 30 minutes to about 10 hours followed by removal of the detergent by conventional methods such as chromatography, to inactivate any viruses present. For example, Horowitz et al. (*Transfusion*, 25 (6):516, 1985) teaches inactivation of viruses using detergents such as tri(n-butyl)phosphate (TNBP) or Tween-80.

In one embodiment, Cohn's fractions II+III supernatant is mixed in a batch adsorption procedure with a solid phase bound heparin, such as heparin-Sepharose (Pharmacia) or heparin-Actigel Superflow (Sterogene) and the suspension is incubated at reduced temperature, that is at or below +3° C., most preferably at 0° to −6° C. Prior to exposure of the solid phase heparin to the plasma fraction, the heparin-Sepharose is washed with an alcoholic solution, for example, a 20% ethanol solution, a preferred alcohol and concentration for use in the instant invention. Another suitable washing solution is a 25% ethanol solution. The heparin-Sepharose then is separated from the liquid phase.

In another embodiment, the heparin-solid phase matrix is packed into a column and the plasma alcoholic fraction is passed over the column. Again, the solid phase heparin is washed prior to and following packing in the column with an alcoholic solution, for example a 20 to 25% ethanol solution.

When the Cohn's fraction II+III supernatant is treated herein at very low temperatures below 4° C., other important proteins found therein, such as albumin, haptoglobin, alpha-1 protease inhibitor, IgA, etc., that might be denatured due to the presence of alcohol at 4° C. or higher are unaffected. Also, the alcohol is useful in preventing freezing of the solid phase at the cold temperatures used in the separation step.

The invention now will be described in the following non-limiting examples.

EXAMPLE 1

Cohn's fractions II+III supernatant was obtained from human plasma as taught in Cohn et al. (*J. Am. Chem. Soc.*, 72, 465 (1950)) at −4° C. to −6° C. Heparin-Actigel Superflow (Sterogene) was washed with a 20% ethanol solution at −4° C. to −6° C. and packed into a 100 ml column at −6° C. Then, 1,500 ml of fraction II+III supernatant was passed over the column.

After the application, the column was washed with 50 ml of 20% ethanol. This wash fraction was processed by Cohn's method to obtain albumin. The column was washed with 0.3M NaCl solution to remove nonspecifically bound proteins. AT-III was eluted with 2M NaCl solution. The AT-III was concentrated by ultrafiltration (Filtron, Omega, 10K).

As a virus inactivation treatment, 1 v/v% of Tween-80 and 0.3 v/v% TNBP were added to the concentrated AT-III solution and incubated at 30° C. for 6 hours. The detergents were removed by ion exchange chromatography (DEAE-Sephadex or heparin affinity chromatography).

The AT-III solution (50 u/ml) was lyophilized under sterile conditions.

The yield of AT-III from Cohn's fractions II+III supernatant was 60% and impurity proteins such as albumin, globulin, transferrin and the like were not detected by electrophoresis on cellulose acetate membrane ((Jowkin, M., et al. *PNAS*, USA 76, 4350 (1978)) and polyacrylamide (Laemmli, U.K., et al. *Nature*, 227, 680 (1970)).

EXAMPLE 2

Two liters of Cohn's fractions II+III supernatant at −4° C. were mixed with 200 ml of heparin-Sepharose (Pharmacia), previously washed with 20% ethanol at −6° C., and the mixture was stirred for 60 minutes at −4° C. The heparin-Sepharose was collected by filtration and washed with 100 ml 20% ethanol at −4° C. and with 500 ml of 0.3M NaCl at −4° C. The AT-III was eluted as described in Example 1.

For virus inactivation, 0.5M sodium citrate was added to the ultrafiltration concentrated AT-III solution. The pH of the solution was adjusted to 7.5 and then the solution was heated at 60° C. for 10 hours. After the heat treatment, the sodium citrate was removed by ultrafiltration.

The AT-III solution (50 u/ml) was lyophilized under sterile conditions.

The AT-III yield from the fraction II and III supernatant was 70% after the heparin treatment and 55% after the heat treatment. Impurity proteins such as albumin, globulin, transferrin and the like were not detected by electrophoresis.

It will be apparent to those skilled in the art that the invention can be modified without departing from the spirit of the instant invention. Any such modifications coming within the spirit and scope of the following claims are considered equivalent thereto.

What is claimed is:

1. A method for obtaining human antithrombin III comprising the steps of:
   (a) obtaining an alcoholic solution of human plasma containing human antithrombin III and 20–25% ethanol;
   (b) exposing said alcoholic solution to solid phase bound heparin to form a mixture at a temperature of between −4° C. to −10° C. and bind antithrombin III to said heparin; and
   (c) separating said solid phase bound heparin from said solution; and
   (d) eluting said human antithrombin III from said bound heparin to obtain an antithrombin III solution.

2. The method of claim 1, wherein said antithrombin III solution is treated to inactive virus.

3. The method of claim 2, wherein said virus inactivation treatment is a heat treatment.

4. The method of claim 2, wherein said virus inactivation treatment is a detergent treatment.

5. The method of claim 1, wherein said alcoholic solution of human plasma is Cohn's fraction II+III supernatant.

6. The method of claim 1, wherein said exposing step (b) is at a temperature of −4° C. to −6° C.

7. The method of claim 1, wherein said exposing step (b) is at a temperature of about −6° C.

8. A method for purifying an alcoholic solution containing human antithrombin III, 20–25% ethanol and other protein comprising the steps of
   (a) exposing said alcoholic solution to solid phase bound heparin to form a mixture at a temperature of between −4° C. to −10° C. and bind antithrombin III to said heparin; and
   (b) separating said solid phase bound heparin from said solution; and
   (c) eluting said human antithrombin III from said bound heparin to obtain a purified antithrombin III solution.

9. The method of claim 8, wherein said alcoholic solution is Cohn's fraction II+III supernatant.

10. The method of claim 9, wherein said exposing step (a) is at a temperature of −4° C. to −6° C.

11. The method of claim 9, wherein said exposing step (a) is at a temperature of about −6° C.

12. The method of claim 9, wherein said solid phase bound heparin is washed with an alcoholic solution prior to said exposing step (a).

13. The method of claim 12, wherein said washing is carried out using a 20 to 25% ethanol solution in water.

14. The method of claim 9, wherein said antithrombin III solution is treated to inactivate virus.

15. The method of claim 14, wherein said virus inactivation comprises a heat treatment or a detergent treatment.

* * * * *

UNITED STATES PATENT AND TRADEMARK OFFICE
CERTIFICATE OF CORRECTION

PATENT NO. : 5,319,072
DATED : June 7, 1994
INVENTOR(S) : Uemura, et al.

It is certified that error appears in the above-indentified patent and that said Letters Patent is hereby corrected as shown below:

Column 1, line 55, delete "IV-VI" and insert -- IV-1 --.

Signed and Sealed this

Seventh Day of March, 1995

Attest:

BRUCE LEHMAN

Attesting Officer          Commissioner of Patents and Trademarks